(12) United States Patent
Daito et al.

(10) Patent No.: US 9,074,461 B2
(45) Date of Patent: Jul. 7, 2015

(54) FLUID ANALYZER WITH PLASMA EMISSION UNIT AND METHOD OF USING SAME

(71) Applicant: Schlumberger Technology Corporation, Sugar Land, TX (US)

(72) Inventors: Shigeo Daito, Yokohama (JP); Tsutomu Yamate, Yokohama (JP); Shunsuke Yamazaki, Yokohama (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 211 days.

(21) Appl. No.: 13/912,157

(22) Filed: Jun. 6, 2013

(65) Prior Publication Data

US 2014/0361155 A1 Dec. 11, 2014

(51) Int. Cl.
| | |
|---|---|
| G01N 21/64 | (2006.01) |
| E21B 49/10 | (2006.01) |
| E21B 49/08 | (2006.01) |
| G01N 27/62 | (2006.01) |
| G01N 27/64 | (2006.01) |

(52) U.S. Cl.
CPC ............... *E21B 49/10* (2013.01); *G01N 27/62* (2013.01); *G01N 27/64* (2013.01); *E21B 49/081* (2013.01)

(58) Field of Classification Search
CPC ............................... E21B 49/10; E21B 49/081
USPC .......................................... 250/256; 166/264
See application file for complete search history.

(56) References Cited

U.S. PATENT DOCUMENTS

| | | | |
|---|---|---|---|
| 7,458,252 | B2 | 12/2008 | Freemark et al. |
| 7,530,265 | B2 | 5/2009 | DiFoggio |
| 2003/0056581 | A1 | 3/2003 | Turner et al. |
| 2009/0128818 | A1 | 5/2009 | Goodwin et al. |
| 2010/0050760 | A1 | 3/2010 | Vannuffelen et al. |
| 2013/0014943 | A1 | 1/2013 | Harrison et al. |
| 2013/0056626 | A1 | 3/2013 | Shen et al. |

FOREIGN PATENT DOCUMENTS

WO 2013/019522 2/2013

OTHER PUBLICATIONS

International search report and written opinion for the equivalent PCT patent application No. PCT/US2014/040984 issued on Sep. 29, 2014.
S. Al-Harthy, et al., "Options for High-Temperature Well Stimulation," Oilfield Review, Winter 2008/2009: 20, No. 4, pp. 52-62.

*Primary Examiner* — Yara B Green
(74) *Attorney, Agent, or Firm* — Daryl R. Wright; Jody DeStefanis

(57) ABSTRACT

A fluid analyzer of a downhole tool positionable in a wellbore penetrating a subterranean formation is provided. The wellbore has a downhole fluid thereabout. The downhole tool has a downhole flowline for receiving the downhole fluid. The fluid analyzer includes a microflowline fluidly coupled to the downhole flowline to receive the downhole fluid therethrough, a plurality of electrodes positionable in the microflowline to generate an electrical field therebetween and to vaporize the downhole fluid passing therebetween whereby plasma emissions are generated from the downhole fluid, and a plasma detector to measure plasma emissions whereby components of the fluid are detectable.

20 Claims, 7 Drawing Sheets

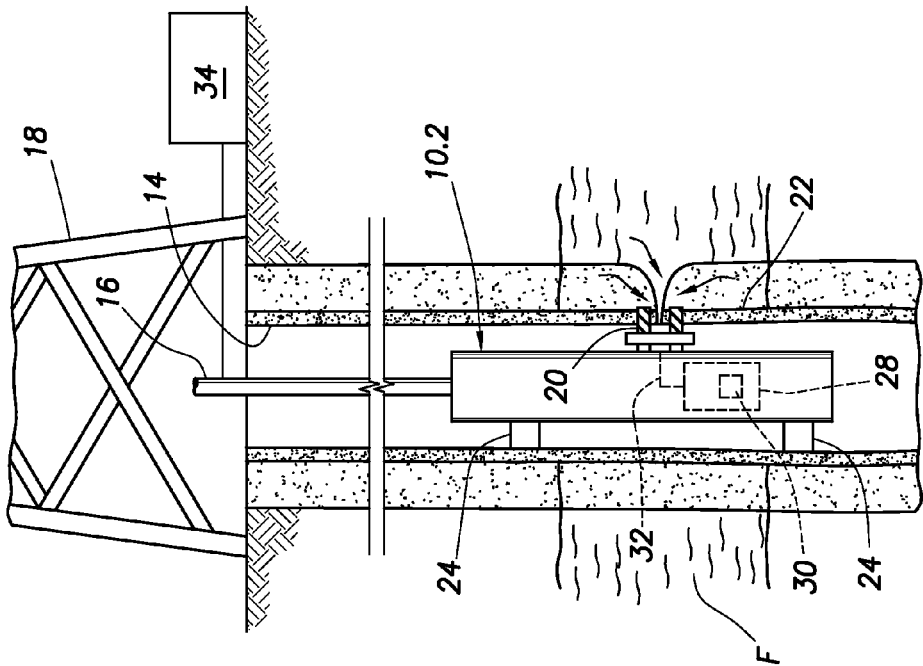
FIG.1.1
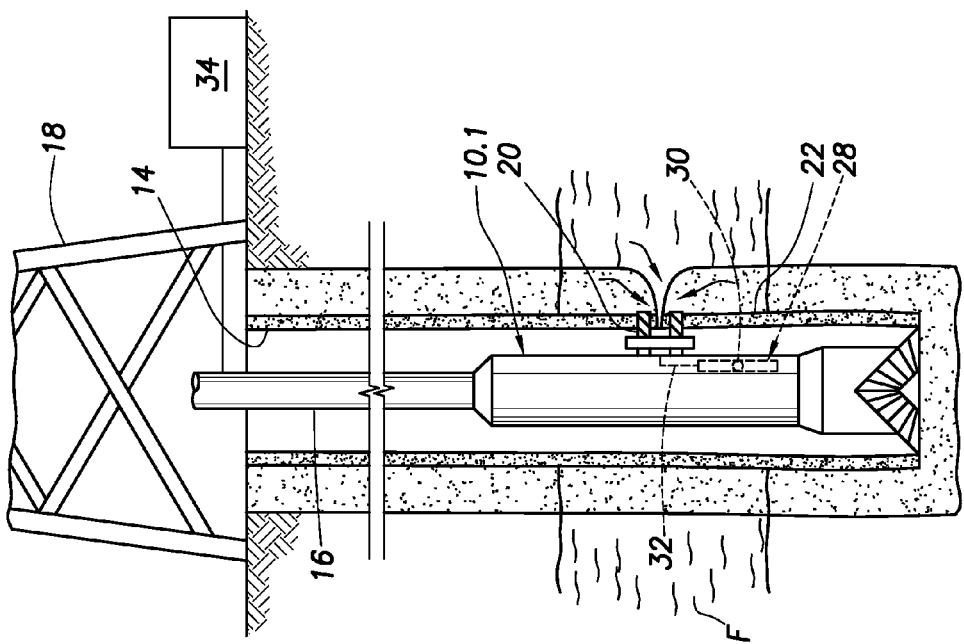
FIG.1.2

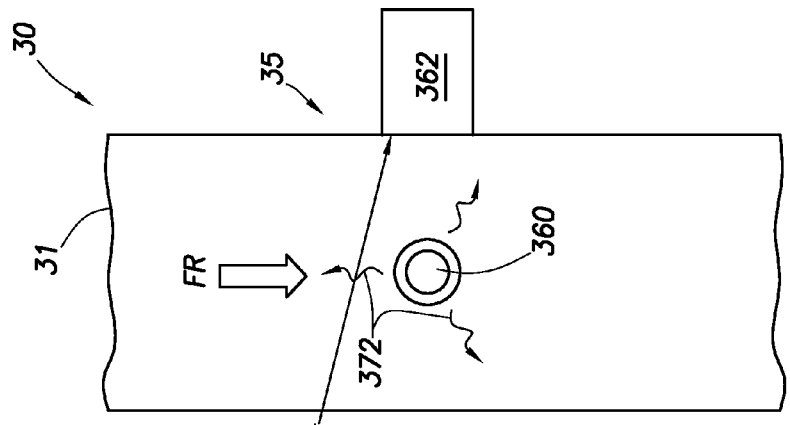
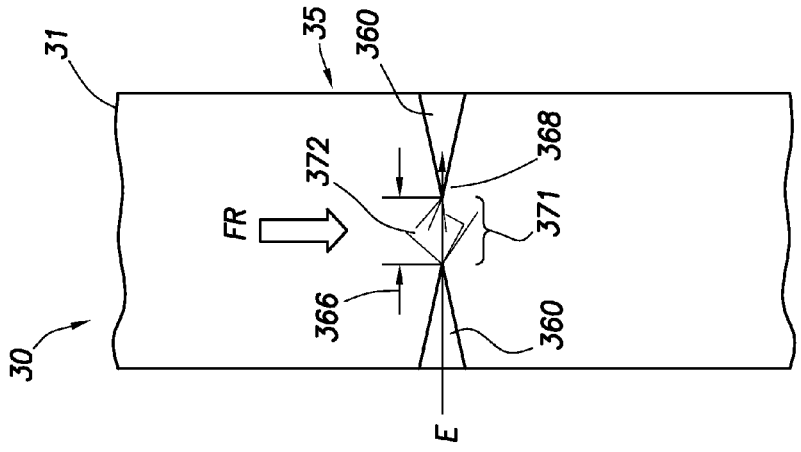
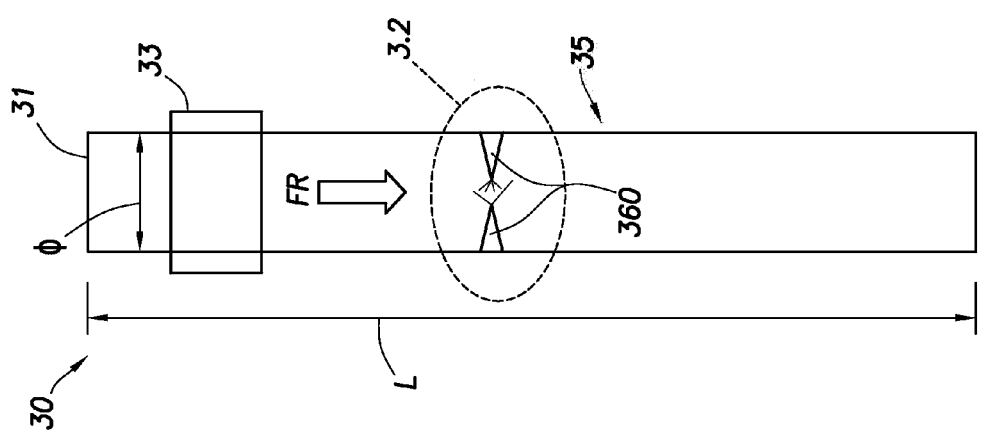

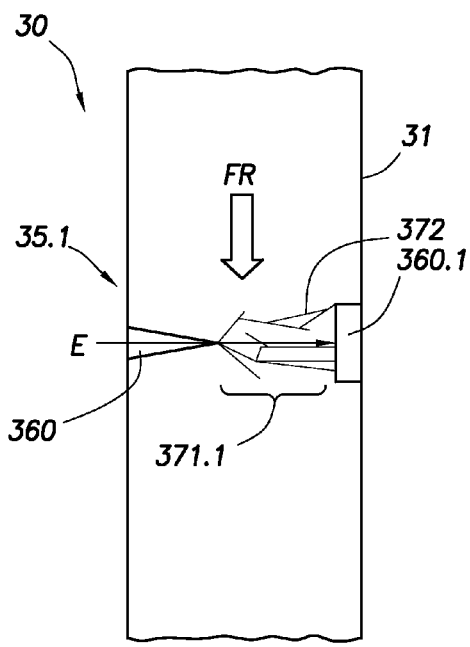
FIG.4.1
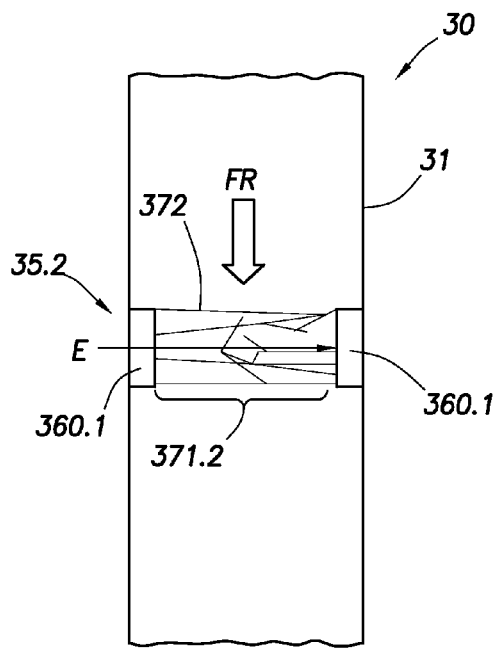
FIG.4.2
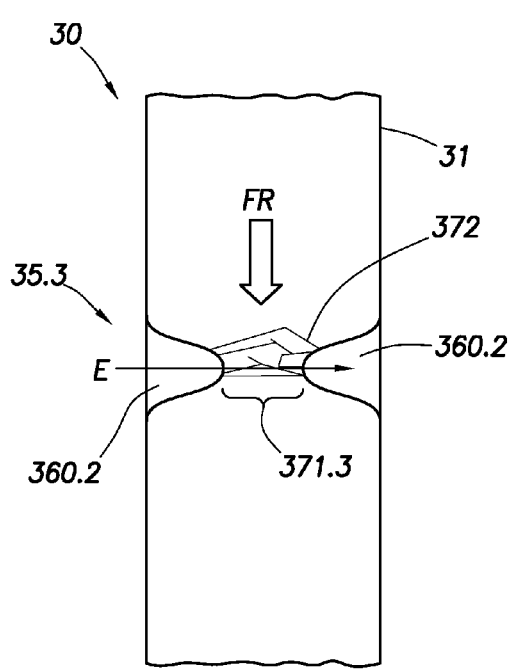
FIG.4.3
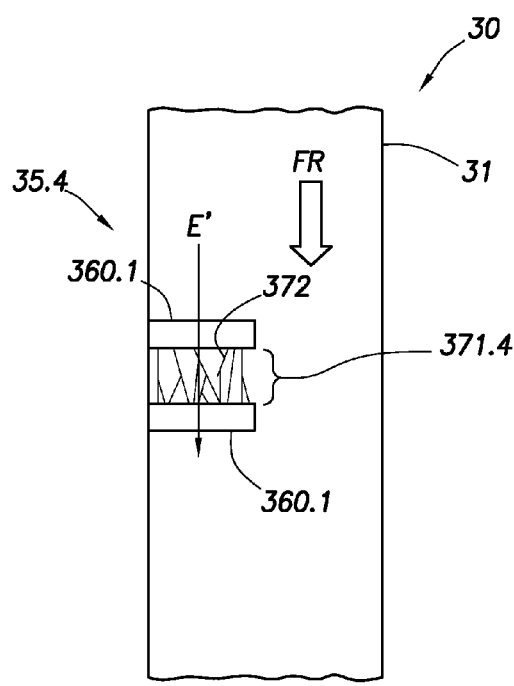
FIG.4.4

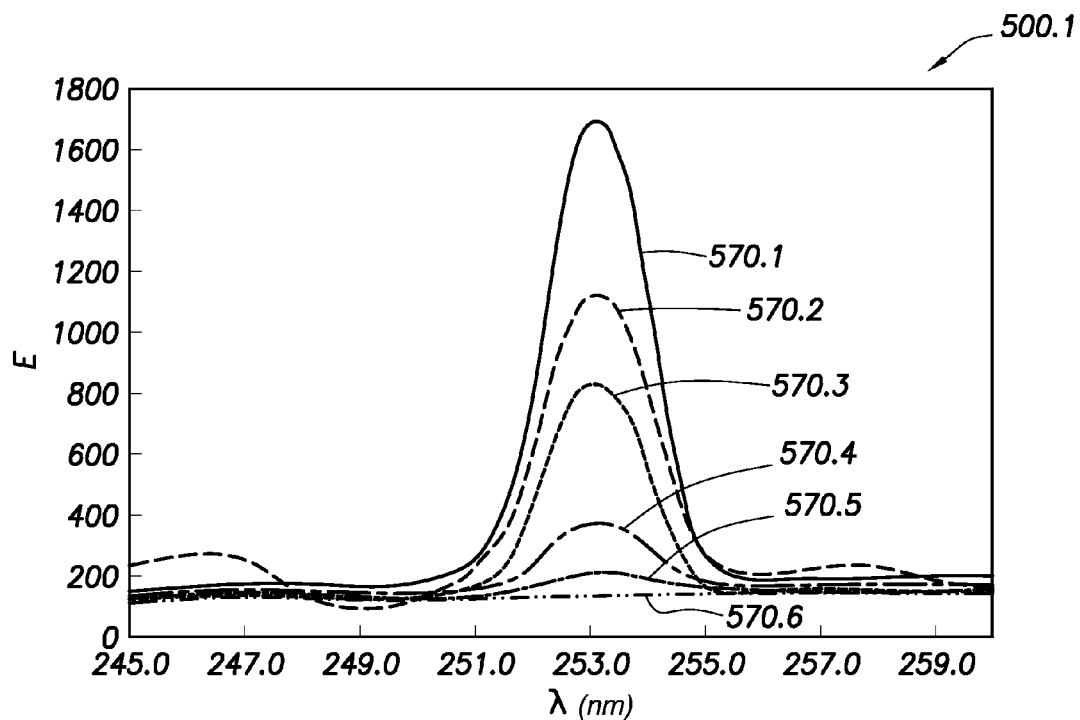
FIG.5.1
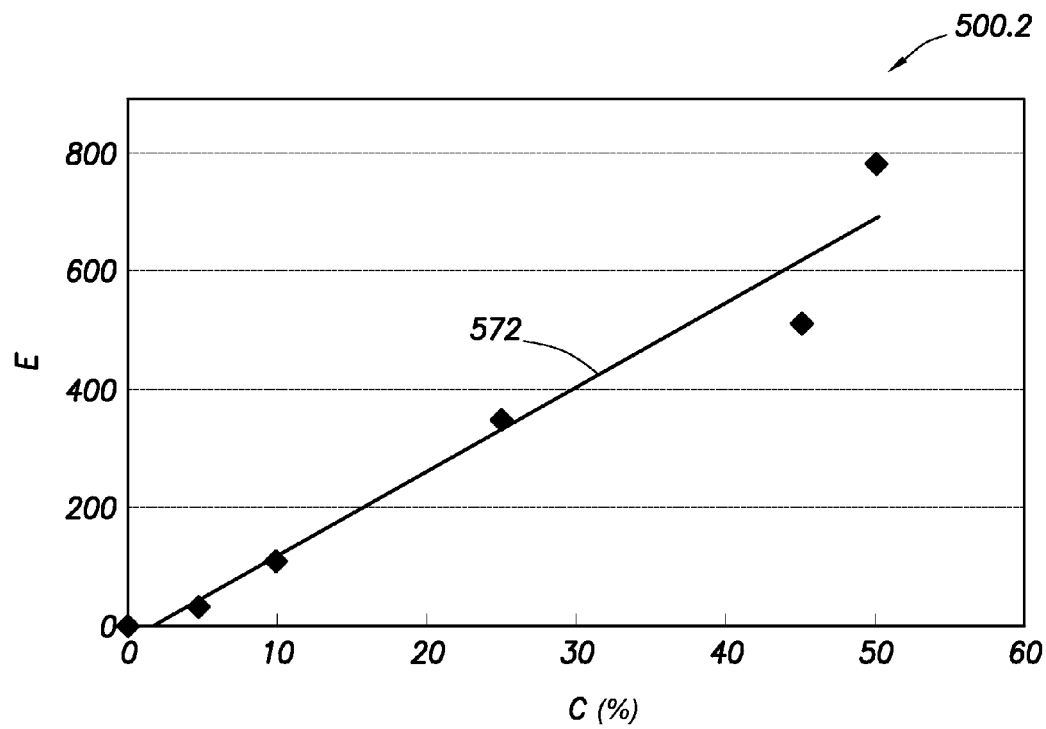
FIG.5.2

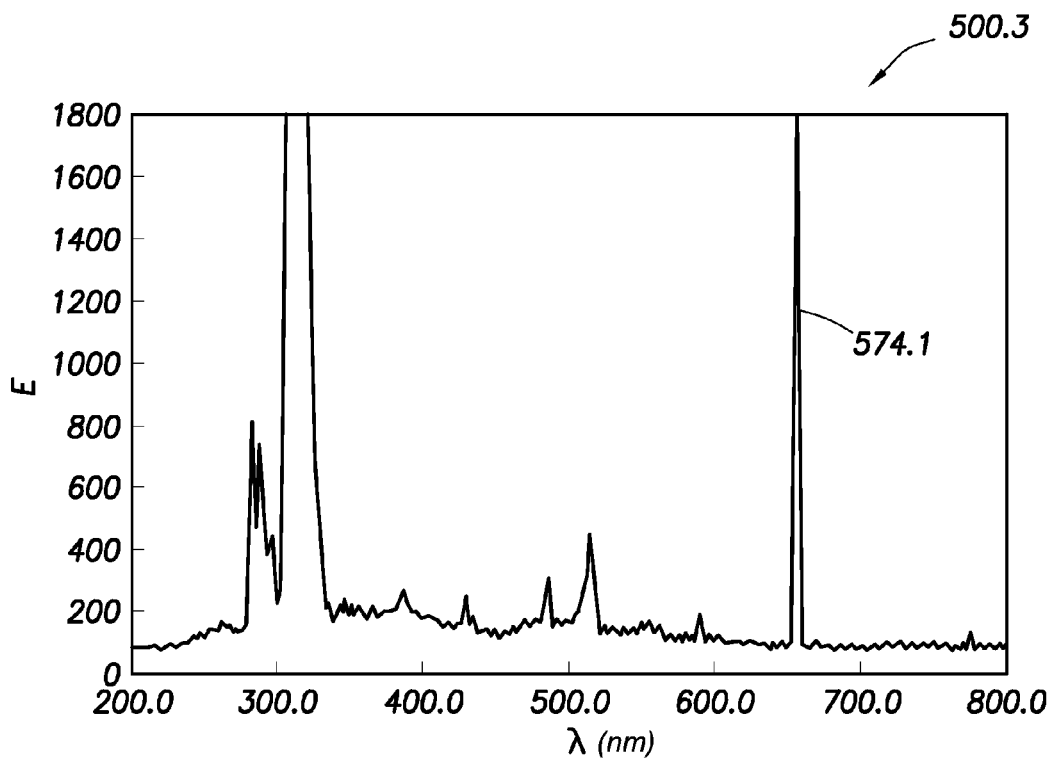
FIG.5.3
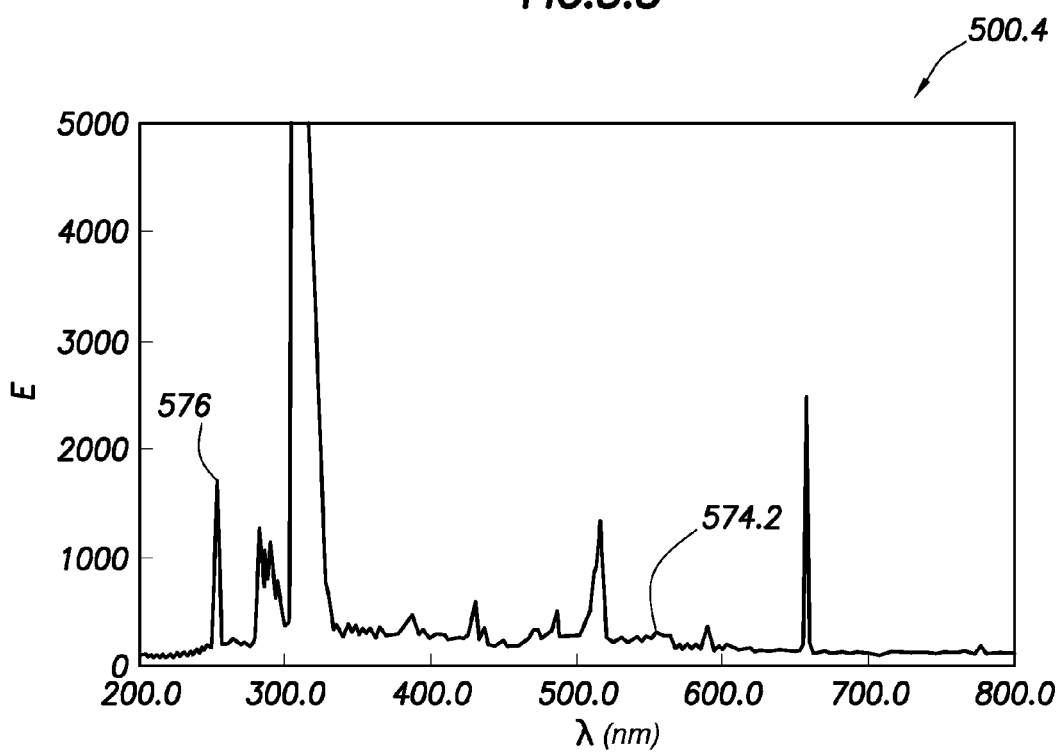
FIG.5.4

US 9,074,461 B2

FLUID ANALYZER WITH PLASMA EMISSION UNIT AND METHOD OF USING SAME

BACKGROUND

The present disclosure relates generally to wellsite operations. In particular, the present disclosure relates to formation evaluation involving downhole devices, such as fluid analyzers and/or plasma detectors.

Wellbores are drilled to locate and produce hydrocarbons. A downhole drilling tool with a bit at an end thereof is advanced into the ground to form a wellbore. As the drilling tool is advanced, a drilling mud is pumped through the drilling tool and out the drill bit to cool the drilling tool and carry away cuttings. The fluid exits the drill bit and flows back up to the surface for recirculation through the drilling tool. The drilling mud is also used to form a mudcake to line the wellbore.

During the drilling operation, various downhole evaluations may be performed to determine characteristics of the wellbore and surrounding formation. In some cases, the drilling tool may be provided with devices to test and/or sample the surrounding formation and/or fluid contained in reservoirs therein. In some cases, the drilling tool may be removed and a downhole wireline tool may be deployed into the wellbore to test and/or sample the formation. These samples or tests may be used, for example, to determine whether valuable hydrocarbons are present.

Formation evaluation may involve drawing fluid from the formation into the downhole tool for testing and/or sampling. Various devices, such as probes or packers, may be extended from the downhole tool to establish fluid communication with the formation surrounding the wellbore and to draw fluid into the downhole tool. Downhole tools may be provided with fluid analyzers and/or sensors to measure downhole parameters, such as fluid properties. Examples of downhole devices are provided in U.S. Patent/Publication Nos. U.S. Pat. No. 7,458,252, U.S. Pat. No. 7,336,356, and US2013/0014943, the entire contents of which are hereby incorporated by reference herein.

SUMMARY

In at least one aspect, the disclosure relates to a fluid analyzer of a downhole tool positionable in a wellbore penetrating a subterranean formation. The wellbore has a downhole fluid thereabout. The downhole tool has a downhole flowline for receiving the downhole fluid. The fluid analyzer includes a microflowline fluidly coupled to the downhole flowline to receive the downhole fluid therethrough, a plurality of electrodes positionable in the microflowline to generate an electrical field therebetween and to vaporize the downhole fluid passing therebetween whereby plasma emissions are generated from the downhole fluid, and a plasma detector to measure plasma emissions whereby components of the downhole fluid are detectable. The microflowline has a diameter and length smaller than a diameter and length of the downhole flowline.

In another aspect, the disclosure relates to a downhole tool positionable in a wellbore penetrating a subterranean formation. The wellbore has a downhole fluid thereabout. The downhole tool includes a housing having a downhole flowline extending therein to receive the downhole fluid, and a fluid analyzer. The fluid analyzer includes a microflowline fluidly coupled to the downhole flowline to receive the downhole fluid therethrough, a plurality of electrodes positionable in the microflowline to generate an electrical field therebetween and to vaporize the downhole fluid passing therebetween whereby plasma emissions are generated from the downhole fluid, and a plasma detector to measure plasma emissions whereby components of the downhole fluid are detectable. The microflowline has a diameter and length smaller than a diameter and length of the downhole flowline.

In yet another aspect, the disclosure relates to a method of analyzing a downhole fluid about a wellbore penetrating a subterranean formation. The method involves positioning a downhole tool with a fluid analyzer therein in the wellbore, receiving the downhole fluid into the downhole tool via a downhole flowline extending therein, receiving a portion of the downhole fluid in a microflowline fluidly coupled to the downhole flowline, generating plasma emissions in the downhole fluid by generating an electrical field between a plurality of electrodes and vaporizing the downhole fluid passing therebetween, and measuring the plasma emissions. The microflowline has a diameter and length smaller than a diameter and length of the downhole flowline.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Embodiments of fluid analyzers with plasma emission unit and method of using same are described with reference to the following figures. The same numbers are used throughout the figures to reference like features and components.

FIGS. 1.1 and 1.2 depict schematic views, partially in cross-section, of a wellsite with a downhole drilling tool and a downhole wireline tool, respectively, deployed into a wellbore for performing downhole formation evaluation in accordance with embodiments of the present disclosure;

FIGS. 3.1-3.3 depict various schematic views of a fluid analyzer having a plasma emission unit with electrodes in a needle-needle configuration in accordance with an embodiment of the present disclosure;

FIGS. 4.1-4.4 depict various schematic views of a fluid analyzer having a plasma emission unit with electrodes in a needle-plate, plate-plate, bump-bump, and an axial plate-plate configuration, respectively, in accordance with an embodiment of the present disclosure;

FIGS. 5.1-5.4 are graphs depicting various measurements taken by a plasma detector of a plasma emission unit in accordance with an embodiment of the present disclosure.

DETAILED DESCRIPTION

Figure 2:
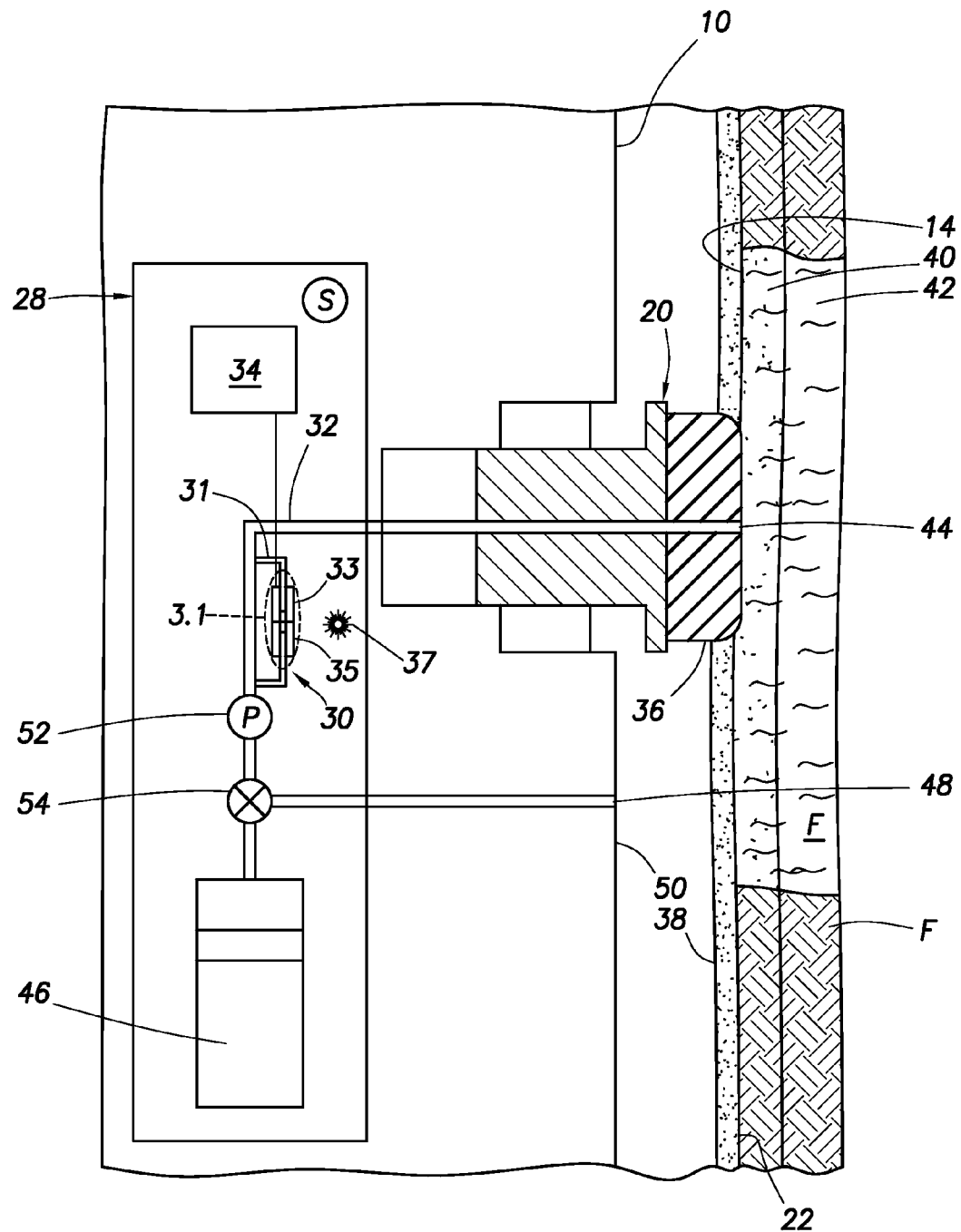
FIG. 2 depicts a schematic view of a portion of a downhole tool having a formation evaluation tool having a fluid analyzer with a plasma emission unit therein in accordance with embodiments of the present disclosure.

The description that follows includes exemplary systems, apparatuses, methods, techniques, and instruction sequences that embody techniques of the inventive subject matter. However, it is understood that the described embodiments may be practiced without these specific details.

The present disclosure relates to formation evaluation involving fluid analysis. In particular, the disclosure describes systems, apparatuses and methods for performing fluid analysis using a plasma emission unit. A fluid analyzer is positionable in a downhole tool and deployable into a wellbore for measuring properties of downhole fluid drawn into the downhole tool. The fluid analyzer includes a microflowline and a plasma emission unit. The plasma emission unit includes electrodes positionable about the microflowline to heat the downhole fluid to a vapor state, to ionize the fluid, and to generate plasma emissions from fluid passing between the electrodes. A photodetector is also provided to measure wavelengths of the plasma emissions which are used to identify materials in the downhole fluid. The electrodes may be positioned in various configurations, such as needle-needle, needle-plate, plate-plate, bump-bump, parallel to fluid flow, perpendicular to fluid flow, etc.

'Formation evaluation' as used herein relates to the measurement, testing, sampling, and/or other analysis of wellsite materials, such as gases, fluids and/or solids. Such formation evaluation may be performed at a surface and/or downhole location to provide data, such as downhole parameters (e.g., temperature, pressure, permeability, porosity, etc.), material properties (e.g., viscosity, composition, density, etc.), and the like.

'Fluid analysis' as used herein relates to a type of formation evaluation of downhole fluids, such as wellbore, formation, reservoir, and/or other fluids located at a wellsite. Fluid analysis may be performed by a fluid analyzer capable of measuring fluid properties, such as viscosity, composition, density, temperature, pressure, flow rate, optical parameters, etc. Fluid analysis may be performed using, for example, optical sensors (e.g., spectrometers), gauges (e.g., quartz), densitometers, viscometers, resistivity sensors, nuclear sensors, plasma detectors, and/or other fluid measurement and/or detection devices.

'Plasma' as used herein refers to a state of matter similar to a gas in which a certain portion of the particles of a material are ionized. Ionization may occur when the material is positioned in a chamber, and the atoms and molecules of the volatilized material are bombarded with electrons in the chamber. The bombardment of the atoms in the material may cause the atoms to emit particles (e.g., photons).

'Plasma emissions' as used herein refers to excited particles (e.g., photons, atoms, ions) generated from the plasma that emit electromagnetic radiation. The radiation may be emitted at wavelengths characteristic of a particular element. The particles may emit radiation at respective wavelengths as the atoms return to their lower energy levels (i.e., their energy levels prior to the excitement).

FIGS. 1.1 and 1.2 depict environments in which subject matter of the present disclosure may be implemented. FIG. 1.1 depicts a downhole drilling tool 10.1 and FIG. 1.2 depicts a downhole wireline tool 10.2 that may be used for performing formation evaluation. The downhole drilling tool 10.1 may be advanced into a subterranean formation F to form a wellbore 14. The downhole drilling tool 10.1 may be conveyed alone or among one or more (or itself may be) measurement-while-drilling (MWD) drilling tools, logging-while-drilling (LWD) drilling tools, or other drilling tools. The downhole drilling tool 10.1 is attached to a conveyor (e.g., drillstring) 16 driven by a rig 18 to form the wellbore 14. The downhole drilling tool 10.1 includes a probe 20 adapted to seal with a wall 22 of the wellbore 14 to draw fluid from the formation F into the downhole drilling tool 10.1 as depicted by the arrows.

The downhole drilling tool 10.1 may be withdrawn from the wellbore 14, and the downhole wireline tool 10.2 of FIG. 1.2 may be deployed from the rig 18 into the wellbore 14 via conveyance (e.g., a wireline cable) 16. The downhole wireline tool 10.2 is provided with the probe 20 adapted to seal with the wellbore wall 22 and draw fluid from the formation F into the downhole wireline tool 10.2. Backup pistons 24 may be used to assist in pushing the downhole wireline tool 10.2 and probe 20 against the wellbore wall 22 and adjacent the formation F.

The downhole tools 10.1, 10.2 may be a formation evaluation tool 28 with a fluid analyzer 30 for analyzing the formation fluid drawn into the downhole tool 10.1, 10.2. The fluid analyzer 30 may have a plasma emission unit capable of generating and detecting plasma emissions in downhole fluids as is described more fully herein. The formation evaluation tool 28 includes a flowline 32 for receiving the formation fluid from the probe 20 and passing the fluid to the fluid analyzer 30 for fluid analysis as will be also described more fully herein. A surface unit 34 may be provided to communicate with the downhole tool 10.1, 10.2 for the passage of signals (e.g., data, power, command, etc.) therebetween. The surface unit 34 may be used, for example, to power the fluid analyzer 30.

While FIGS. 1.1 and 1.2 depict specific types of downhole tools 10.1 and 10.2, any downhole tool capable of performing formation evaluation may be used, such as drilling, coiled tubing, wireline or other downhole tool. Also, while FIGS. 1.1 and 1.2 depict the fluid analyzer 30 in a wellbore 14, it will be appreciated that the fluid analyzer 30 may be at a surface and/or downhole location at the wellsite, and/or at an offsite facility for analyzing the fluid.

By positioning the fluid analyzer 30 in the downhole tool, real-time data may be collected in situ at downhole conditions (e.g., temperatures and pressures where formation evaluation is performed) where downhole fluids are located and/or calibrations performed. Fluids may also be evaluated at surface and/or offsite locations. Fluid samples may also be taken to a surface and/or offsite location, and analyzed in one or more fluid analyzers, such as fluid analyzer 30. Data and test results from various locations and/or using various methods and/or apparatuses may be analyzed and compared.

FIG. 2 is a schematic view of a portion of a downhole tool 10, which may be either of the downhole tool 10.1 or 10.2 of FIG. 1.1 or 1.2. The probe 20 may be extended from the downhole tool 10 for engagement with the wellbore wall 22. The probe 20 is provided with a packer 36 for sealing with the wellbore wall 22. Packer 36 contacts the wellbore wall 22 and forms a seal with a mudcake 38 lining the wellbore wall 22. A mud filtrate of the mudcake 38 seeps into the wellbore wall 22 and creates an invaded zone 40 about the wellbore 14. The invaded zone 40 contains the mud filtrate and other wellbore fluids that may contaminate surrounding formations, such as formation F, and a portion of clean formation fluid 42 from the formation F.

The formation evaluation tool 28 may be provided with one or more downhole flowlines 32 for drawing fluid into the downhole tool 10 through an inlet 44 in the probe 20. While one probe 20 with one inlet 44 is depicted, one or more probes, dual packers and related inlets may be provided to receive downhole fluids and pass them to one or more downhole flowlines 32. Examples of downhole tools and fluid communication devices, such as probes, that may be used are depicted in U.S. Pat. No. 7,458,252, previously incorporated by reference herein.

The downhole flowline 32 extends into the downhole tool 10 to pass downhole fluid to the formation evaluation tool 28.

The formation evaluation tool 28 may be used to analyze, test, sample and/or otherwise evaluate the downhole fluid.

The fluid analyzer 30 is positioned in the formation evaluation tool 28 and is coupled to the downhole flowline 32 for receiving the downhole fluid. A sample chamber 46 is also coupled to the downhole flowline 32 for receiving the downhole fluid. Fluid collected in the sample chamber 46 may be collected therein for retrieval at the surface, or may be exited through an outlet 48 in housing 50 of the downhole tool 10.

One or more sensors S may optionally be provided to measure various downhole parameters and/or fluid properties. The sensor(s) may include, for example, gauges (e.g., quartz), densitometers, viscometers, resistivity sensors, nuclear sensors, and/or other measurement and/or detection devices capable of taking downhole data relating to, for example, downhole conditions and/or fluid properties.

Optionally, flow of the downhole fluid into and/or through the downhole tool 10 may be manipulated by one or more flow control devices, such as a pump 52, the sample chamber 46, valves 54 and/or other devices. Optionally, a surface and/or downhole unit 34 may be provided to communicate with the formation evaluation tool 28, the fluid analyzer 30, and/or other portions of the downhole tool 10 for the passage of signals (e.g., data, power, command, etc.) therebetween.

The fluid analyzer 30 is positioned in the formation evaluation tool 28 and coupled to the downhole flowline 32 for receiving the downhole fluid. The fluid analyzer 30 includes a microflowline 31, a fluid separator 33 and a plasma emission unit 35. An optional light source 37 may also be provided.

The microflowline 31 may be fluidly coupled to the downhole flowline 32 for receiving a portion of the downhole fluid therefrom. As shown, the microflowline 31 is coupled to the downhole flowline 32 at an upstream and a downstream location to form a continuous loop. This loop permits a portion of downhole fluid from the downhole flowline 32 to pass through the microflowline 31 and return to the downhole flowline 32. Fluid may flow through the microflowline 31 at a desired flow rate. Flow control devices, such as pump 52, sample chamber 46, valve 54 and/or other devices may be provided to manipulate flow through the downhole flowline 32 and/or microflowline 31.

FIGS. 3.1-3.3 schematically depict a portion 3.1 of the fluid analyzer 30 of FIG. 2 in greater detail. FIG. 3.1 shows a portion 3.1 of the plasma fluid analyzer 30 depicting the microflowline 31 and the plasma emission unit 35. FIG. 3.2 shows a front view of a portion 3.2 of the plasma emission unit 35 of FIG. 3.1 in greater detail. FIG. 3.3 shows a side view of the plasma emission unit 35 of FIG. 3.2.

As shown in FIG. 3.1, the microflowline 31 has a diameter (or width) φ and a length L. The diameter φ and the length L may be selected to permit a small volume of fluid to divert from the downhole flowline 32 at a flow rate FR to pass through the plasma emission unit 35. The downhole flowline 32 (FIG. 2) may have, for example, a diameter of about 5 mm, a length of from about 1 m to about 100 m, and a flow rate of from about 10 to about 100 cc/min The microflowline 31 may have a diameter of from about 0.001 mm to about 1 mm, a length of from about 0.01 m to about 1 m, a flow rate of from about 0.1 to about 1 cc/min, and a volume of about 10 μl.

The downhole fluid passing into the microflowline 31 may include various components, such as oil, water, gases, etc. A fluid separator 33 may optionally be provided to separate the downhole fluid into various components. The fluid separator 33 may be any suitable fluid separator capable of removing select components from the fluid. An example of a cyclone separator is provided in WO2013/019522. The fluid may be separated to provide desired fluids to the plasma emission unit 35 for measurement. For example, the fluid separator 33 may be used to separate hydrocarbons and/or other materials from the downhole fluid to permit the passage of water to the plasma emission unit 35 for measurement.

The plasma emission unit 35 includes a pair of electrodes 360 mounted in microflowline 31. The electrodes 360 may be, for example, anode and cathode electrodes. The electrodes 360 may be conductive electrodes capable of generating sufficient conductivity to ionize the downhole fluid of the plasma emission unit 35. Examples of electrodes are provided in US2013/0014943, previously incorporated by reference herein.

The electrodes 360 may be positioned along the microflowline 31 on opposite sides thereof with a flow gap 366 for passage of fluid therebetween. The flow gap 366 may be, for example a distance of from about 0.001 mm to about 1 mm. The electrodes 360 each have an end 368 extending from opposite walls of the microflowline 31. As shown in FIG. 3.2, the electrodes 360 have pointed ends 368 which provide a needle-to-needle configuration for measurement therebetween. A narrow, horizontal plasma volume 371 is defined therebetween.

The electrodes 360 may be used to generate heat to the downhole fluid passing therebetween. The downhole fluid is vaporized from liquid to gas by heat from the electrodes 360. Optionally, light may be emitted from light source 37 (if provided) to heat and vaporize the downhole fluid. Under heat, the downhole fluid eventually becomes ionized and generates plasma emissions 372 about the electrodes 360.

The electrodes 360 generate a field E extending horizontally therebetween in a direction perpendicular to the flow of the fluid as schematically indicated by the arrow. The electrodes 360 provide electric conductivity to generate the plasma emissions 372 from the downhole fluid. Electric conductivity may be used to generate plasma emission from a variety of conductive downhole fluids, such as water.

Wavelengths of the plasma emissions 372 generated by the electrodes 360 are measureable by a plasma detector 362. The plasma detector 362 may be, for example, a spectrometer capable of measuring wavelengths of the plasma emissions 372. Other detectors may be used, such as resistivity sensors, or other detectors capable of detecting plasma emission of the downhole fluid. Examples of detectors are provided in US2013/0014943, previously incorporated by reference herein. Light from light source 37 passing through the fluid may also be measured and analyzed. Various optical parameters (e.g., wavelength) may be determined from the light for analysis.

Plasma emissions 372 may be used to identify monoatomic particles using specific wavelength of light detection, since each atom has a specific wavelength of light emission based on an electron potential when energy is applied thereto. Thus, the measured wavelengths of the plasma particles may be used for identification of materials in the fluid. For example, materials, such as lead, mercury and other metals may be detected. The plasma detector 362 may be used with, for example, an optics filter to select specific wavelengths for detection.

By way of example, the plasma detector 362 may measure the wavelengths of the plasma emissions 372 (e.g., photons) to determine the presence of particular atoms corresponding to those wavelengths. Spectroscopic methods may then be used to accurately identify atoms, molecules, substances or fluid components such as, but is not limited to mercury, nickel, vanadium, sulfur, radon, polonium, barium, strontium, nitrogen, calcium, oxygen, helium, methane, ethane, propane, etc. in fluid samples and the concentrations of those atoms, molecules, substances, or fluid components and/or atomic concentrations.

Intensity of the emitted wavelengths or the size-to-mass ratio (in the case of mass spectrometry) may be measured to determine concentrations of those atoms. In addition to determining atomic concentration(s), detecting the presence of a particular atom in a fluid sample may be indicative of the presence of a particular molecule. For example, detecting the presence and concentration of sulfur (S) atoms can be indicative of the presence and concentration of hydrogen sulfide ($H_2S$) in a fluid sample as well as other thiols (mercaptans, hydrosulfides, thiolates, mercaptides) that may be sufficiently volatile to vaporize into a gaseous portion of a depressurized sample.

As shown by FIGS. 3.1-4.4, the fluid analyzer 30 may have plasma emission units 35-35.4 with various configurations for generating desired plasma emissions. The needle-needle configuration of the electrodes 360 of FIGS. 3.1-3.3 provides a focused electrical field E between the ends 368 for generating plasma emissions therebetween. This needle-needle configuration provides a narrow horizontal plasma volume 371 for plasma generation. This focused volume may use a limited amount of power, and provide a narrow band for measurement.

As shown in FIGS. 3.1-4.4, the size of the plasma volume may be varied by varying the size and shape of the electrodes. For example, as shown in the plasma emission unit 35.1 of FIG. 4.1, a needle electrode 360 is paired with a plate electrode 360.1 to provide a needle-plate interface for generating plasma emissions 372 therebetween. A plasma volume 371.1 is defined between the electrodes 360 and 360.1. This needle-plate configuration provides a tapered, horizontal plasma volume 371.1 for plasma generation.

As shown in the plasma emission unit 35.2 of FIG. 4.2, two plate electrodes 360.1 provide a plate-plate interface for generating plasma emissions 372 therebetween. A wide (or thick) linear plasma volume 371.2 is defined between the plate electrodes 360.1.

Other variations may be used to alter the shape, measurement area, and/or power usage. For example, as shown in the plasma emission unit 35.3 of FIG. 4.3, a pair of bump electrodes 360.2 has a bump shape to provide a bump-bump interface for generating plasma emissions 372 therebetween. A plasma volume 371.3 is defined between the bump electrodes 360.2. As depicted, the plasma volume 371.3 is narrow in the middle and widens at upstream and downstream ends thereabout.

As shown in the plasma emission unit 35.4 of FIG. 4.4, the electrodes may be positioned in various locations along the microflowline 31. A pair of plate electrodes 360.1 is positioned on one side of the microflowline 31 with the fluid passing thereby. The pair of plate electrodes 360.1 is positioned along the microflowline 31 to define a field E' that is parallel to the flow of fluid through the microflowline 31 as schematically indicated by the arrow. The pair of plate electrodes 360.1 is also positioned to define plasma volume 371.4 therebetween. As shown, the plasma volume 371.4 has the same shape as the plasma volume 371.2 of FIG. 4.2, but in an axial configuration parallel to the fluid flow.

The shape, type and/or location of the electrodes may be configured to generate the desired plasma emissions. The plasma emissions generated in the fluid passing through the electrodes 360-360.2 may be altered to focus or increase the amount of emissions generated therebetween. Electrodes with smaller ends may be selected to provide a more focused measurement and to reduce power usage. Electrodes with larger ends may be selected to provide a broader area for measurement at an increased power usage. Various combinations of one or more electrodes may be provided in the microflowline 31 to provide the desired quality, power usage, and/or measurement volume for generating the plasma emissions.

FIGS. 5.1-5.4 depict graphs 500.1-500.4 depicting example measurements taken by plasma emission units 35-35.4. The data may be gathered using, for example, an atomic emission analyzer, such as MH-5000 commercially available from MICRO EMISSION™ (see http://www.micro-emission.com/index.html).

The graph 500.1 of FIG. 5.1 plots intensity of emission (E) (y-axis) versus wavelength ($\lambda$) (x-axis) for various fluids. As shown by FIG. 5.1, various materials are detected by the plasma emissions, such as various amounts of mercury (Hg) and/or other materials as designated by lines 570.1-570.6. In the example shown, line 570.1 has about 50 ppm of mercury, line 570.2 has about 45 ppm mercury with about 10% heptane, line 570.3 has about 25 ppm mercury with about 50% methanol, line 570.4 has about 10 ppm of mercury, line 570.5 has about 5 ppm mercury with 50% methanol, and line 570.6 is blank. As demonstrated by this graph, increased amounts detected present a larger plasma emission on the graph.

The graph 500.2 of FIG. 5.2 plots intensity of emission (E) (y-axis) versus concentration (C) of Hg (x-axis) for various fluids. As shown by FIG. 5.2, various materials are detected by the plasma emissions, such as various amounts of mercury (Hg) as designated by line 572. These measurements may be, for example, one shot measurements for a liquid containing various chemicals.

The graph 500.3 of FIG. 5.3 plots intensity of emission (E) (y-axis) versus wavelength ($\lambda$) (x-axis) for various fluids. The graph 500.4 of FIG. 5.4 plots intensity of emission (E) (y-axis) versus wavelength ($\lambda$) (x-axis) for various chemical substances of the fluid. As shown by FIGS. 5.3 and 5.4, various materials may be detected by the plasma emissions. As shown by line 574.1 of FIG. 5.3, no mercury is detected. As shown by line 574.2 of FIG. 5.4, mercury is detected at point 576. Point 576 may be enlarged as shown by line 570.1 in FIG. 5.1.

Other measurements and outputs may optionally be generated based on measurements taken by the plasma detector.

Figure 6:
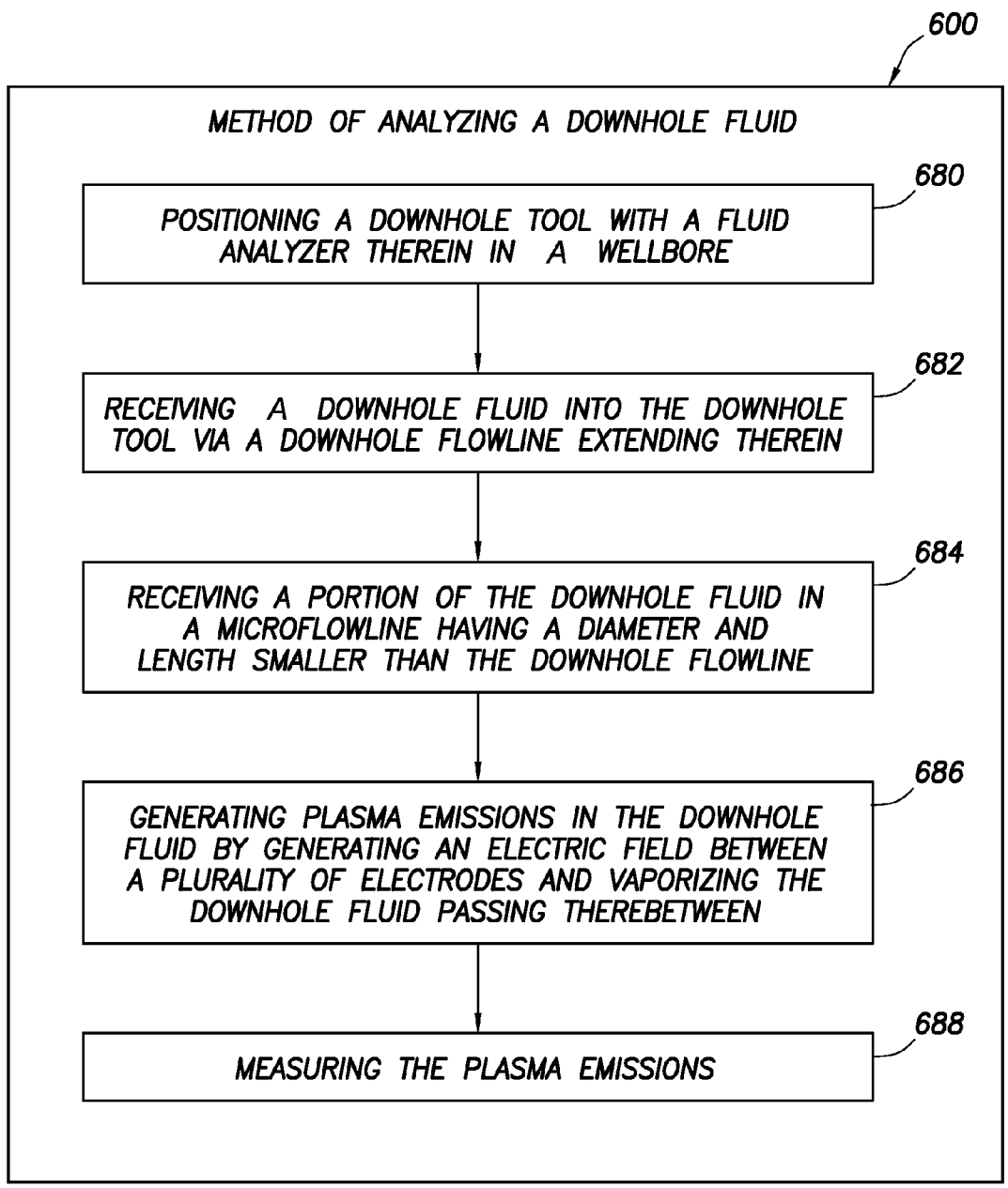
FIG. 6 is a flow chart depicting a method of analyzing a downhole fluid in accordance with embodiments of the present disclosure.

FIG. 6 shows a flow chart 600 of a method of analyzing a downhole fluid. The method 600 involves positioning (680) a downhole tool with a fluid analyzer therein in a wellbore, receiving (682) a downhole fluid into the downhole tool via a downhole flowline extending therein, receiving (684) a portion of the downhole fluid in a microflowline fluidly coupled to the downhole flowline (the microflowline having a diameter and length smaller than a diameter and length of the downhole flowline), generating (686) plasma emissions in the downhole fluid by generating an electrical field between a plurality of electrodes and vaporizing the downhole fluid passing therebetween, and measuring (688) the plasma emissions.

The method may also involve identifying at least one component of the downhole fluid from the plasma emissions, and/or emitting a light through the downhole fluid and measuring optical parameters of the light. The method may be performed in any order and repeated as desired.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A fluid analyzer of a downhole tool positionable in a wellbore penetrating a subterranean formation, the wellbore having a downhole fluid thereabout, the downhole tool having a downhole flowline for receiving the downhole fluid, the fluid analyzer comprising:
    a microflowline fluidly coupled to the downhole flowline to receive the downhole fluid therethrough, the microflowline having a diameter and length smaller than a diameter and length of the downhole flowline;
    a plurality of electrodes positionable in the microflowline to generate an electrical field therebetween and to vaporize the downhole fluid passing therebetween whereby plasma emissions are generated from the downhole fluid; and
    a plasma detector to measure the plasma emissions whereby components of the downhole fluid are detectable.

2. The fluid analyzer of claim 1, wherein the microflowline has a diameter of from about 0.001 mm to about 1 mm.

3. The fluid analyzer of claim 1, wherein the microflowline has a length of from about 0.01 m to about 1 m.

4. The fluid analyzer of claim 1, wherein at least one of the plurality of electrodes has a needle end.

5. The fluid analyzer of claim 1, wherein at least one of the plurality of electrodes has a plate end.

6. The fluid analyzer of claim 1, wherein at least one of the plurality of electrodes has a bump end.

7. The fluid analyzer of claim 1, wherein the plurality of electrodes are positioned on opposite sides of the microflowline.

8. The fluid analyzer of claim 1, wherein the electrical field is generated in a direction parallel to a flow of the downhole fluid through the microflowline.

9. The fluid analyzer of claim 1, wherein the electrical field is generated in a direction perpendicular to a flow of the downhole fluid through the microflowline.

10. The fluid analyzer of claim 1, further comprising a light source to emit light through the downhole fluid passing between the plurality of electrodes, the light measurable by the plasma detector.

11. The fluid analyzer of claim 1, further comprising a fluid separator.

12. A downhole tool positionable in a wellbore penetrating a subterranean formation, the wellbore having a downhole fluid thereabout, the downhole tool comprising:
    a housing having a downhole flowline extending therein to receive the downhole fluid; and
    a fluid analyzer, comprising:
        a microflowline fluidly coupled to the downhole flowline to receive the downhole fluid therethrough, the microflowline having a diameter and length smaller than a diameter and length of the downhole flowline;
        a plurality of electrodes positionable in the microflowline to generate an electrical field therebetween and to vaporize the downhole fluid passing therebetween whereby plasma emissions are generated from the downhole fluid; and
        a plasma detector to measure the plasma emissions whereby components of the downhole fluid are detectable.

13. The downhole tool of claim 12, further comprising a probe.

14. The downhole tool of claim 12, further comprising a sensor.

15. The downhole tool of claim 12, further comprising a control unit.

16. The downhole tool of claim 12, further comprising a pump.

17. The downhole tool of claim 12, further comprising a sample chamber.

18. A method of analyzing a downhole fluid about a wellbore penetrating a subterranean formation, the method comprising:
    positioning a downhole tool with a fluid analyzer therein in the wellbore;
    receiving the downhole fluid into the downhole tool via a downhole flowline extending therein;
    receiving a portion of the downhole fluid in a microflowline fluidly coupled to the downhole flowline, the microflowline having a diameter and length smaller than a diameter and length of the downhole flowline;
    generating plasma emissions in the downhole fluid by generating an electrical field between a plurality of electrodes and vaporizing the downhole fluid passing therebetween; and
    measuring the plasma emissions.

19. The method of claim 18, further comprising identifying at least one component of the downhole fluid from the plasma emissions.

20. The method of claim 18, further comprising emitting a light through the downhole fluid and measuring optical parameters of the light.

* * * * *